United States Patent [19]

Kenna

[11] Patent Number: 4,714,469
[45] Date of Patent: Dec. 22, 1987

[54] SPINAL IMPLANT

[75] Inventor: Robert V. Kenna, Hobe Sound, Fla.

[73] Assignee: Pfizer Hospital Products Group, Inc., New York, N.Y.

[21] Appl. No.: 19,283

[22] Filed: Feb. 26, 1987

[51] Int. Cl.$^4$ .......................... A61F 2/44; A61F 5/04; A61B 17/00

[52] U.S. Cl. .................... 623/17; 128/92 YM; 128/92 VY; 128/92 VD; 128/92 VL; 128/303 R

[58] Field of Search ..................... 623/16–18, 623/20; 128/69, 92 YM, 92 V, 92 VY, 92 VD, 92 VL, 303 R, 305

[56] References Cited

U.S. PATENT DOCUMENTS

| D. 245,259 | 8/1977 | Shen | 623/20 X |
|---|---|---|---|
| 3,867,728 | 2/1975 | Stubstad et al. | 623/17 |
| 4,364,389 | 12/1982 | Keller | 128/303 R |
| 4,450,834 | 5/1984 | Fischer | 128/92 VL X |
| 4,550,448 | 11/1985 | Kenna | 623/16 |

FOREIGN PATENT DOCUMENTS

| 0179695 | 4/1986 | European Pat. Off. | 623/17 |
|---|---|---|---|
| 695664 | 11/1979 | U.S.S.R. | 128/92 V |
| 1132930 | 1/1985 | U.S.S.R. | 128/92 V |

Primary Examiner—Ronald L. Frinks
Attorney, Agent, or Firm—Peter C. Richardson; Lawrence C. Akers; Mark Dryer

[57] ABSTRACT

A spinal implant adapted to replace a disc between adjacent vertebrae having a predetermined thickness and profile chosen to match the space between said vertebrae and characterized by elongated protuberances adapted to be located in grooves drilled in said vertebrae and a porous coating on at least a portion of its surface. A method and apparatus for placement of said spinal implant are also disclosed.

9 Claims, 16 Drawing Figures

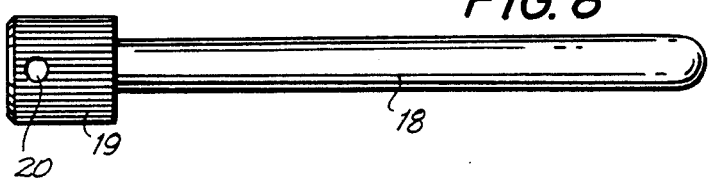
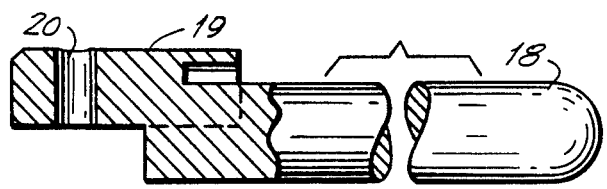
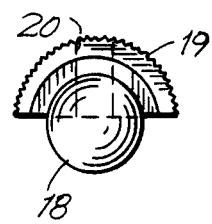
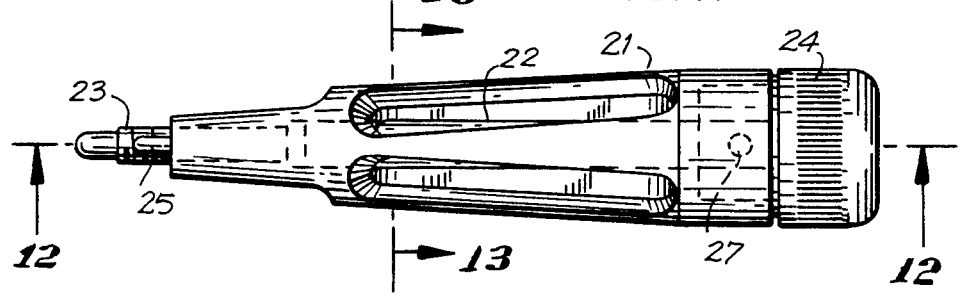
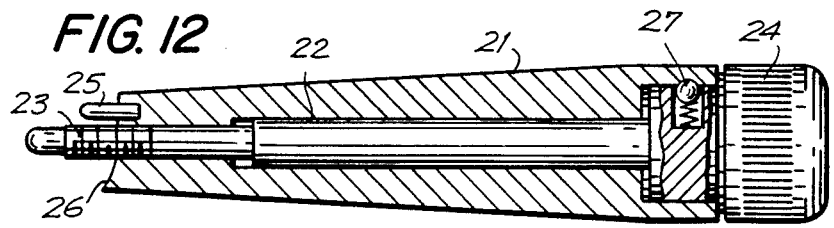
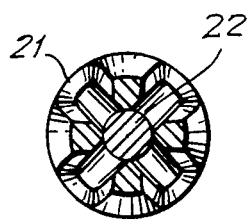

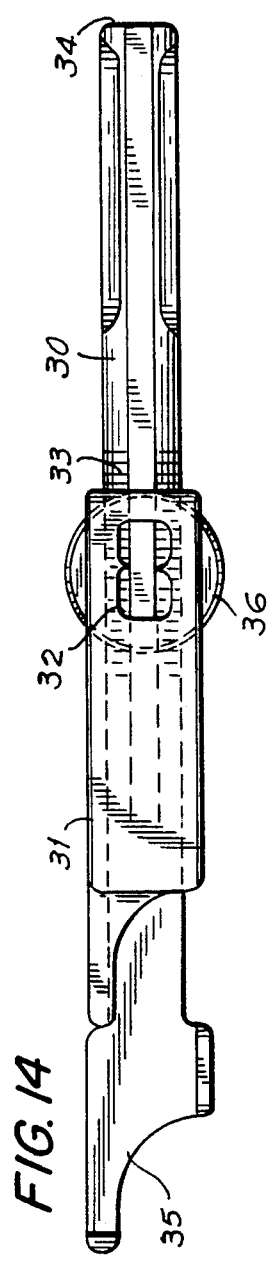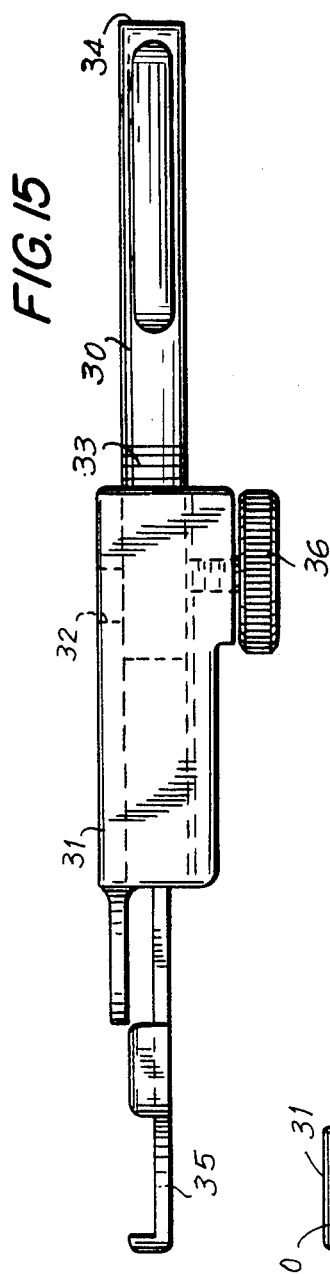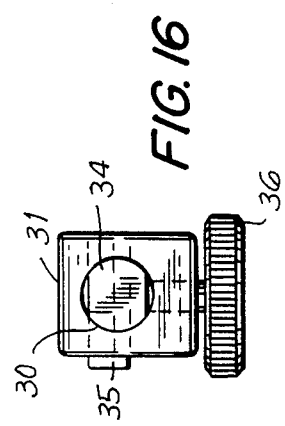

SPINAL IMPLANT

BACKGROUND OF THE INVENTION

This invention relates to a spinal implant, particularly an implant adapted to encourage bone ingrowth resulting in stabilization of adjacent vertebrae and reduction of back pain. The invention is also concerned with a method of implantation and an apparatus for placement of the spinal implant between adjacent vertebrae.

Many types of intervertebral implants are known in the art. For example, U.S. Pat. No. 3,867,728 discloses a prosthesis for spinal repair which comprises a laminated core element made from an elastomer, such as silicone rubber or polyurethane, and fabric-reinforced elastomer.

U.S. Pat. No. 4,309,777 discloses an artificial intervertebral disc comprising upper and lower disc portions having a plurality of springs positioned therebetween and spikes extending outwardly from said disc portions for engagement with adjacent upper and lower vertebrae.

U.S. Pat. No. 4,349,921 discloses an intervertebral disc prosthesis comprising a shaped body of substantially rigid, non-porous, biologically compatible material. The surfaces of the disc have characteristics to produce a "friction-fit".

U.S. Pat. No. 4,479,491 discloses an intervertebral stabilization implant including an elongated central portion and a pair of reverse wings each disposed at an angle with respect to the elongated central portion.

Other types of spinal stabilizers, for example fixator plates and rods, are also known in the art, but these are not intervertebral implants as that term is used herein.

It has now been found that improved stabilization is achieved by an implant which is adapted to encourage bone ingrowth and thereby stabilizes adjacent vertebrae by fusing said vertebrae to the implant.

SUMMARY OF THE INVENTION

In accordance with the present invention there is provided a spinal implant comprising a rigid solid body having a first surface, a second surface and a third surface of predetermined thickness between and perpendicular to said first and second surfaces, each of said first and second surfaces being defined by a substantially D-shaped profile the curved portion of which conforms to the outer profile of the vertebrae between which the implant is adapted to be implanted, said predetermined thickness being chosen to correspond to the space between said vertebrae, each of said first and second surfaces having an elongated protuberance of substantially semi-circular cross-section extending the full width of the surface parallel to the straight side of the D, and at least a portion of each first and second surface having a porous coating thereon.

Preferably, said porous coating is applied to each of said protuberances.

In a preferred embodiment of the invention a threaded hole and an adjacent locking hole are located in said third surface parallel to the straight side of the D, for holding said implant and placing it in position between vertebrae.

The rigid solid body of the implant according to the invention preferably is made from a high strength, biocompatible, corrosion-resistant, cobalt-chromium-molybedenum alloy and the porous coating comprises two layers of substantially spherical particles of the same or similar alloy as the body. A particularly suitable alloy of this type is that known by the registered Trade Mark "Vitallium".

The invention also provides a method of placing a spinal implant as described above between adjacent upper and lower vertebrae in a spinal column, which comprises removing the disc between said vertebrae, measuring the resulting space between said vertebrae, placing in said space a drill guide having dimensions matching said space, drilling semi-cylindrical grooves in the upper and lower vertebrae, which grooves are positioned by use of said guide to match with complimentary protuberances in the implant, removing said drill guide and inserting a spinal implant of predetermined thickness which matches said space by locating the protuberances on the implant in the pre-drilled grooves in the upper and lower vertebrae.

In the performance of said method, preferably the integrity of the space to receive the implant is maintained by appropriate spacers prior to insertion of the implant.

The invention further provides a method of replacing a degenerate disc between adjacent upper and lower vertebrae in a spinal column, which comprises inserting two spinal implants in side by side relationship in the space formed by removal of said disc according to the method described above.

The invention still further provides an apparatus for placement of a spinal implant between adjacent upper and lower vertebrae in a spinal column, which comprises:

(a) a drill guide comprising an elongated arm with a distal end, a proximal end, an upper surface and a lower surface, said proximal end being attached to a handle, semi-cylindrical grooves extending from said distal end to said proximal end in both the upper surface and the lower surface, each of said grooves being adapted to accommodate a drill bit of predetermined diameter;

(b) at least one drill bit of predetermined diameter;

(c) a measuring device associated with or incorporated in said drill guide comprising a linear gauge adapted to measure the depth of the drill bore in the vertebrae and stop means for preventing further drilling when the desired depth is achieved;

(d) two spacers, each comprising an elongated arm having the same diameter as said drill bit of predetermined diameter, said arm being attached at its proximal end to a handle;

(e) a positioning tool comprising an elongated member with a distal end, a proximal end and an axial bore throughout its length, a cylindrical member with a distal end and a proximal end located in said axial bore, the distal end of said cylindrical member being threaded and being adapted to be screwed into a threaded hole located in a spinal implant, the proximal end of said cylindrical member being attached to a knurled knob for turning said cylindrical member to screw or unscrew said threaded distal end and a cylindrical locking key extending from the distal end of said elongated member adjacent and parallel to said threaded axial cylindrical member, which locking key is adapted to slide into a locking hole in a spinal implant. Preferably, the distal end of said elongated member is shaped to match the profile of a spinal implant for which it is to be used.

DESCRIPTION OF THE DRAWINGS

The invention will be more particularly described with reference to a preferred embodiment as illustrated in the accompanying drawings, in which:

FIG. 8 is a side view of a spacer for an apparatus according to the invention;

FIG. 9 is a detail of the proximal end of said spacer of FIG. 8;

FIG. 10 is an end view of said spacer;

FIG. 11 is a top view of a positional tool for an apparatus according to the invention;

FIG. 12 is a side view of said positioning tool;

FIG. 13 is a section through line 13—13 of FIG. 11; and

FIGS. 14–16 illustrate a measuring device used in the apparatus of the invention.

DETAILED DESCRIPTION OF THE INVENTION

Figure 2:
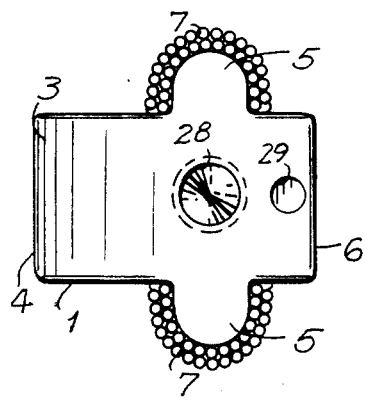
FIG. 2 is an end elevation of the implant of FIG. 1.
Figure 1:
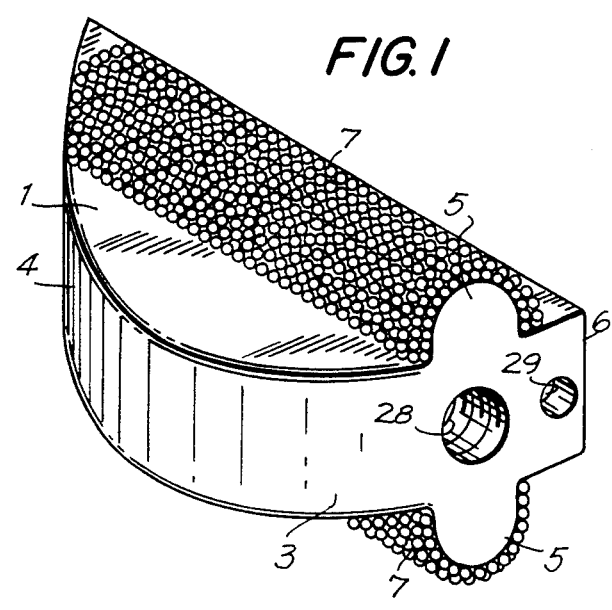
FIG. 1 is a perspective view of a spinal implant according to the invention.
Figure 3:
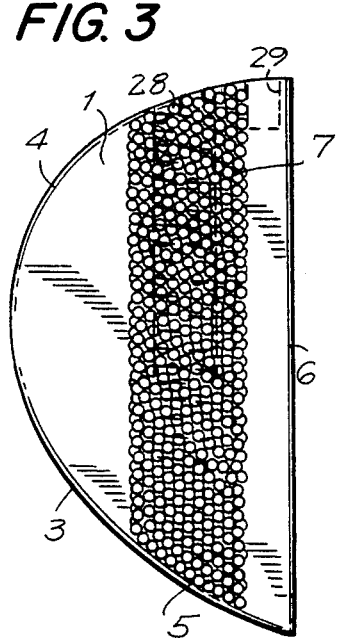
FIG. 3 is a side elevation of the implant of FIG. 1.

Referring to the drawings, FIGS. 1–3 illustrate a preferred spinal implant according to the invention. Said implant comprises a rigid solid body having a first surface 1 and a second surface 2. A third surface 3 of predetermined thickness is between and perpendicular to said first and second surfaces. Each of said first and second surfaces is defined by a substantially D-shaped profile whose curved portion 4 conforms to the outer profile of the vertebrae between which the implant is adapted to be implanted (see FIG. 4). The predetermined thickness of the third surface 3 is chosen to correspond to the space between the vertebrae in which the implant is to be implanted, said thickness corresponding substantially to that of the healthy disc which originally occupied said space. When a disc between adjacent vertebrae is removed prior to placement of an implant according to the invention, the resultant space between the vertebrae is carefully measured and an implant of appropriate thickness is chosen for the subsequent implantation.

Each of the first and second surfaces 1, 2 of the implant has an elongated protuberance 5 of substantially semi-circular cross-section extending the full width of said surface parallel to the straight side 6 of the D.

In the preferred embodiment illustrated in FIGS. 1–3 the surface of each of said protuberances 5 has a porous coating 7 thereon.

The rigid solid body of the preferred embodiment, i.e. the body defined by the above described surfaces, is made from a high strength, biocompatible, corrosion-resistant cobalt-chromium-molybdenum alloy, for example "Vitallium", and said porous coating preferably comprises two layers of substantially spherical particles of the same or similar alloy as the body. A particularly suitable porous coating is that disclosed in commonly assigned U.S. Pat. No. 4,550,448, the disclosure of which is incorporated herein by reference.

In alternative embodiments of the invention, the porous coating may extend over all or part of the first and second surfaces 1, 2 in addition to the surface of the protuberances. However, it has been found that a porous coating over the protuberances only (as illustrated in the drawings) is normally sufficient to provide adequate bone ingrowth to stabilize the vertebrae. The third surface 3 does not come into direct contact with bone and is not porous coated.

A prime object of the porous coated spinal implant of the invention is to eliminate back pain associated with loss of joint space secondary to a back fusion procedure. The implant is designed to stabilize the vertebrae following debridement of a disc. After placement of the implant between adjacent vertebrae tissue/bone ingrowth into the porous coating provides long-term stability. The various thicknesses of the implants are chosen to reconstitute the disc space between the vertebrae, thus preventing pressure from developing about the dura and/or nerve roots relative to the collapse of said disc space.

The protuberances, which extend anterior to posterior, provide rotational stability. This is clearly illustrated in FIG. 4 which shows two implants placed in side by side relationship in the space formed by removal of a disc between two adjacent vertebrae 8,8. The use of separate implants allows replacement of the disc without interfering with the spinal cord. The space 9 between the implants will eventually be filled with ingrowth of tissue or bone.

FIGS. 5–16 of the drawings illustrate components of the preferred apparatus used for placement of the spinal implant of the invention.

Figure 5:
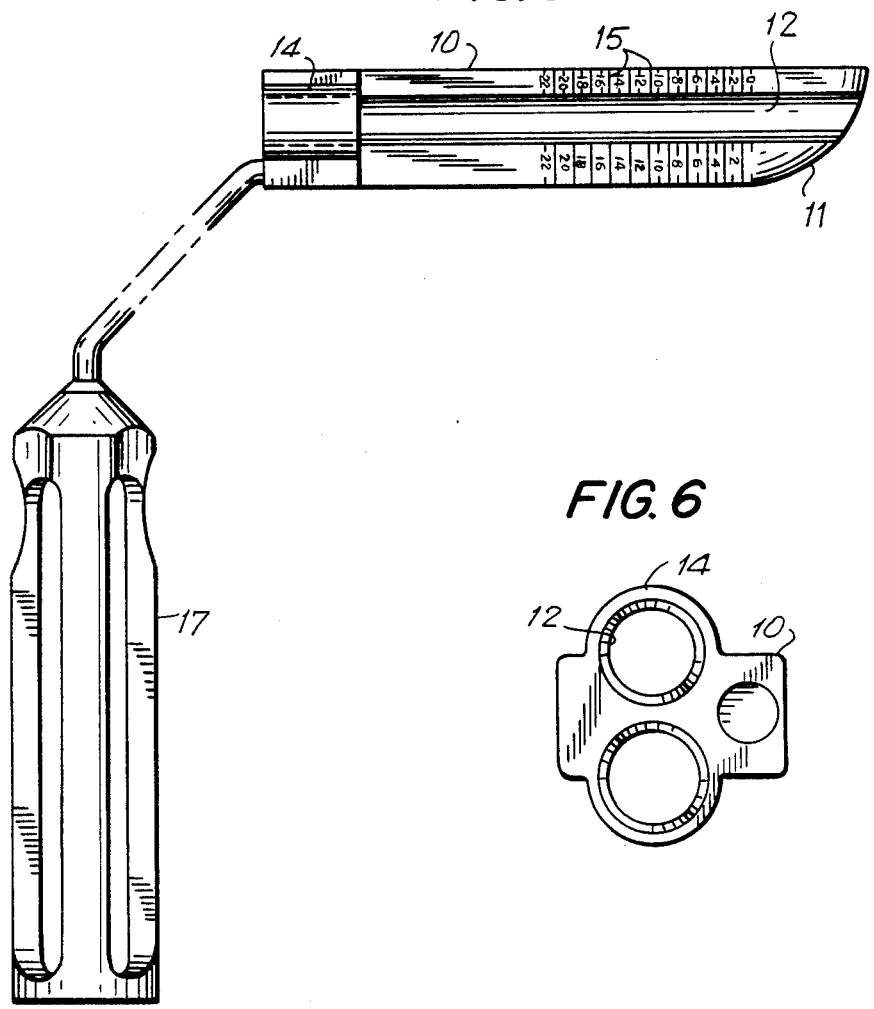
FIG. 5 is a top view of a drill guide for an apparatus according to the invention.
Figure 6:
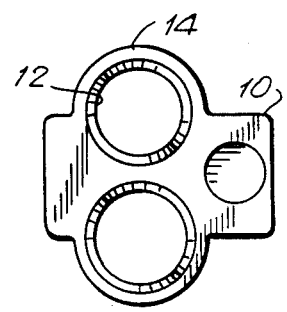
FIG. 6 is an end view of said drill guide.
Figure 7:
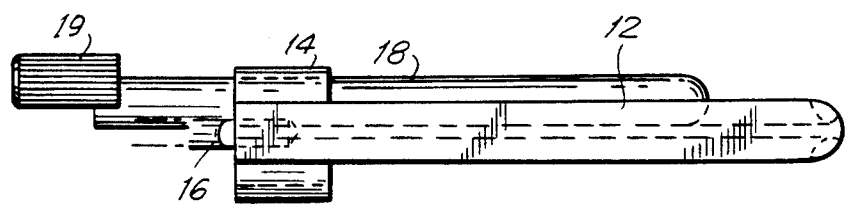
FIG. 7 is a side view of said drill guide.

The apparatus comprises a drill guide, illustrated in FIGS. 5–7; spacers, illustrated in FIGS. 7–10; a positioning tool, illustrated in FIGS. 11–13 and a measuring device illustrated in FIGS. 14–16.

The drill guide illustrated in FIGS. 5–7 comprises an elongated arm 10 having a distal end 11 which is shaped to match the profile of the spinal implant for which the apparatus is to be used. The drill guide has an upper surface and a lower surface and FIG. 5 is a top plan view showing the upper surface a semi-cylindrical groove 12 extends from the distal end to the proximal end of each of the upper surface and the lower surface. Each of the grooves 12 is adapted to accommodate a drill bit (not shown) of predetermined diameter.

The drill bit enters the groove and is rotatably held therein through a circular arch at the proximal end of the guide. Each groove also is adapted to accommodate a spacer comprising an elongated arm 18 (FIG. 7) having the same diameter as said drill bit of predetermined diameter.

Both surfaces of the drill guide have equally spaced linear markings 15 which give an indication of the depth to which the guide should be inserted and are used in conjunction with the marking device described below with reference to FIGS. 14–16.

The elongated arm of the drill guide is attached through an angled rigid arm 16 to a handle 17. The angle is such that the axis of the handle is substantially perpendicular to the axis of the elongated arm. This configuration provides satisfactory clearance for insertion of the drill bits and spacers and still allows the drill guide to be held in a stable manner during the drilling operation.

As shown in FIGS. 8–10 the elongated arm 18 of each spacer has, at its distal end, a knurled member 19 which acts as a handle to insert and remove the spacer. The knurled handle includes a bore 20 through which a pin may be inserted to stabilize both spacers when in place.

FIGS. 11–13 illustrate a positioning tool which comprises an elongated member 21 having an axial bore in which is located a cylindrical member 22. The distal end of said cylindrical member has a thread 23 which is adapted to be screwed into a threaded hole 28 (see FIG. 4) in a spinal implant. The proximal end of the cylindrical member is attached to a knurled knob 24 for turning said cylindrical member to screw or unscrew said threaded distal end. A cylindrical locking key 25 extends from the distal end of the elongated member adjacent and parallel to the threaded distal end of the axial cylindrical member. This locking key is adapted to slide into a locking hole 29 (FIG. 4) in a spinal implant. This prevents rotation of the implant about the axis of the positioning tool.

Preferably the distal end 26 of the elongated member is shaped to match the curved profile of the spinal implant for which it is to be used.

The cylindrical member 22 is adapted to be removed from the elongated member and is held in place therein by a spring-loaded ball bearing 27 which seats into a cooperating groove running around the internal periphery of the elongated member as shown in FIG. 12.

The measuring device used in the apparatus of the invention operates as a simple caliper device which measures the depth of the vertebrae.

As shown in FIGS. 14–16, the measuring device comprises a calibrated arm 30 which slides within an outer sleeve 31. The sleeve has an aperture 32 through which depth calibration lines 33 may be viewed.

Prior to drilling, in order to determine the correct depth for drilling the distal end 34 of the calibrated arm is placed between the vertebrae and its position is adjusted by appropriate sliding movement through a handle 35 at the proximal end. When the depth of the vertebra is determined the calibrated arm is locked within the sleeve by screwing the knurled knob 36 of a locking screw. The correct depth is shown by the calibration line in the aperture 32 and this reading is matched with a corresponding reading in the markings 15 on the drill guide. Thereby the correct depth for drilling is obtained.

In order to replace a degenerate disc, the disc is first removed by a known surgical technique, leaving a space between the adjacent upper and lower vertebrae. The space is maintained, i.e. the vertebrae are prevented from collapsing, before and after drilling by a standard laminar spreader.

To prepare the space for insertion of side-by-side implants according to the invention appropriate grooves must be drilled in the upper and lower vertebrae.

First and correct depth is determined with the measuring device described above and each drill guide is calibrated accordingly. Then a drill guide is inserted to the correct depth on one side of the vertebrae after removal of the laminar spreader. Grooves in the upper and lower vertebrae are then drilled using a drill bit of the appropriate predetermined diameter. Said diameter matches the diameter of the protuberance of the correct implant for the replaced disc.

When the grooves are drilled each drill bit is removed and replaced by a spacer to maintain the spaces between the vertebrae.

This operation is repeated on the other side of the vertebrae.

Each drill guide and attached spacers is then sequentially removed and replaced by a laminar spreader to prevent collapse of the vertebrae and, at the same time, leaving clearance for insertion of the two implants.

Figure 4:
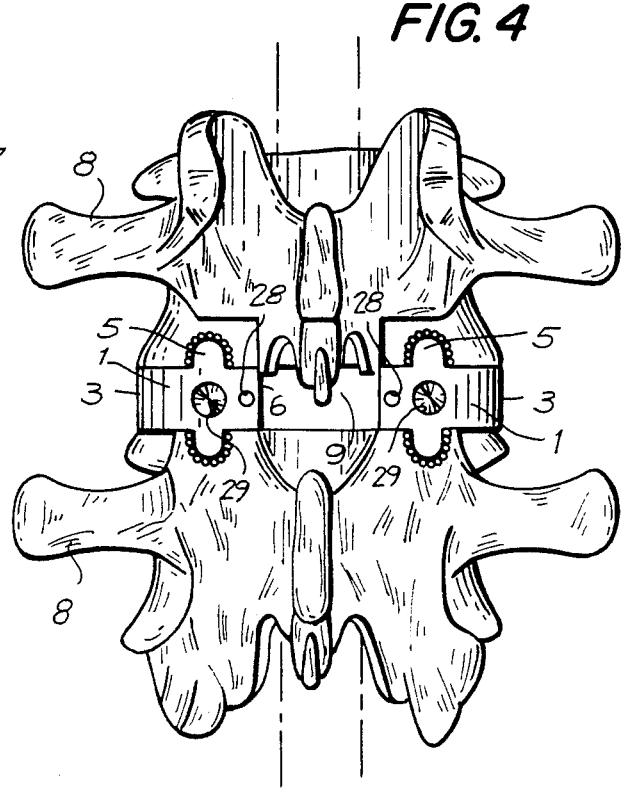
FIG. 4 is a perspective view showing two implants of the invention in place between two adjacent vertebrae.

The implants are inserted sequentially with the aid of the appropriate positioning tool and when each implant is properly in place between the vertebrae the positioning tool is unscrewed therefrom by turning the knurled knob and removed. When the implant is inserted the laminar spreader may be removed. The placement of the implants is as shown in FIG. 4.

I claim:

1. A spinal implant comprising a rigid solid body having a first surface, a second surface and a third surface of predetermined thickness between and perpendicular to said first and second surfaces, each of said first and second surfaces being defined by a substantially D-shaped profile the curved portion of which conforms to the outer profile of the vertebrae between which the implant is adapted to be implanted, said predetermined thickness being chosen to correspond to the space between said vertebrae, each of said first and second surfaces having an elongated protuberance of substantially semi-circular cross-section extending the full width of the surface parallel to the straight side of the D, and at least a portion of each first and second surface having a porous coating thereon.

2. An implant according to claim 1, in which said porous coating is applied to each of said protuberances.

3. An implant according to claim 1, in which a threaded hole and an adjacent locking hole are located in said third surface parallel to the straight side of the D, for holding said implant and placing it in position between vertebrae.

4. An implant according to claim 1, in which the rigid solid body is made from a high strength, biocompatible, corrosion-resistant, cobalt-chromium-molybdenum alloy and the porous coating comprises two layers of substantially spherical particles of the same or similar alloy as the body.

5. A method of placing a spinal implant according to claim 1 between adjacent upper and lower vertebrae in a spinal column, which comprises removing the disc between said vertebrae, measuring the resulting space between said vertebrae, placing in said space a drill guide having dimensions matching said space, drilling semi-cylindrical grooves in the upper and lower vertebrae, which grooves are positioned by use of said guide to match with complimentary protuberances in the implant, removing said drill guide and inserting a spinal implant of predetermined thickness which matches said space by locating the protuberances on the implant in the pre-drilled grooves in the upper and lower vertebrae.

6. A method according to claim 5, wherein the integrity of the space to receive the implant is maintained by appropriate spacers prior to insertion of the implant.

7. A method of replacing a degenerate disc between adjacent upper and lower vertebrae in a spinal column, which comprises inserting two spinal implants in side by side relationship in the space formed by removal of said disc according to the method of claim 5.

8. An apparatus for placement of a spinal implant between adjacent upper and lower vertebrae in a spinal column, which comprises:

(a) a drill guide comprising an elongated arm with a distal end, a proximal end, an upper surface and a lower surface, said proximal end being attached to a handle, semi-cylindrical grooves extending from said distal end to said proximal end in both the upper surface and the lower surface, each of said grooves being adapted to accommodate a drill bit of predetermined diameter;

(b) at least one drill bit of predetermined diameter;

(c) a measuring device associated with or incorporated in said drill guide comprising a linear gauge adapted to measure the depth of the drill bore in the vertebrae the stop means for preventing further drilling when the desired depth is achieved;

(d) two spacers, each comprising an elongated arm having the same diameter as said drill bit of predetermined diameter, said arm being attached at its proximal end to a handle;

(e) a positioning tool comprising an elongated member with a distal end, a proximal end and an axial bore throughout its length, a cylindrical member with a distal end and a proximal end located in said axial bore, the distal end of said cylindrical member being threaded and being adapted to be screwed into a threaded hole located in a spinal implant, the proximal end of said cylindrical member being attached to a knurled knob for turning said cylindrical member to screw or unscrew said threaded distal end and a cylindrical locking key extending from the distal end of said elongated member adjacent and parallel to said threaded axial cylindrical member, which locking key is adapted to slide into a locking hole in a spinal implant.

9. An apparatus according to claim 8 in which the distal end of said elongated member is shaped to match the profile of a spinal implant for which it is to be used.

* * * * *